United States Patent
Tihon et al.

(10) Patent No.: US 6,895,972 B2
(45) Date of Patent: May 24, 2005

(54) INCONTINENCE DEVICE INSERTION KIT

(75) Inventors: Claude Tihon, Eden Prairie, MN (US); Mark A. Rydell, Golden Valley, MN (US); Alan P. Lonneman, Plymouth, MN (US); Lloyd R. Armstrong, Golden Valley, MN (US)

(73) Assignee: ContiCare Medical, Inc., Eden Prairie, MN (US)

( * ) Notice: Subject to any disclaimer, the term of this patent is extended or adjusted under 35 U.S.C. 154(b) by 0 days.

(21) Appl. No.: 10/838,430

(22) Filed: May 3, 2004

(65) Prior Publication Data

US 2004/0200482 A1 Oct. 14, 2004

Related U.S. Application Data

(62) Division of application No. 10/146,087, filed on May 15, 2002, now Pat. No. 6,739,341.

(51) Int. Cl.[7] ................................................ A61F 5/48
(52) U.S. Cl. ............... 128/885; 128/869; 128/DIG. 25; 600/29; 600/30; 600/31
(58) Field of Search ................................ 128/885, 869, 128/DIG. 25; 600/29, 30, 31

(56) References Cited

U.S. PATENT DOCUMENTS

| | | | |
|---|---|---|---|
| 3,372,695 A | | 3/1968 | Beliveau et al. |
| 3,646,929 A | * | 3/1972 | Bonnar ........................ 600/29 |
| 3,705,575 A | * | 12/1972 | Edwards ...................... 600/29 |
| 4,290,420 A | * | 9/1981 | Manetta ........................ 600/29 |
| 5,749,826 A | * | 5/1998 | Faulkner ...................... 600/29 |
| 5,792,042 A | * | 8/1998 | Cohen et al. ................. 600/29 |
| 5,813,974 A | * | 9/1998 | Dolade Guardia ........... 600/29 |
| 6,311,689 B1 | * | 11/2001 | Tihon .......................... 128/885 |
| D459,470 S | * | 6/2002 | James ......................... D24/105 |
| 6,460,542 B1 | * | 10/2002 | James ......................... 128/885 |
| 6,500,194 B2 | * | 12/2002 | Benderev et al. ........... 606/232 |
| 6,558,312 B2 | * | 5/2003 | Latour, Jr. ................... 600/29 |
| 6,638,211 B2 | * | 10/2003 | Suslian et al. ................ 600/30 |
| 6,652,450 B2 | * | 11/2003 | Neisz et al. .................. 600/30 |
| 6,685,623 B2 | * | 2/2004 | Presthus et al. ............. 600/29 |
| 6,685,629 B2 | * | 2/2004 | Therin ......................... 600/37 |
| 6,695,763 B2 | * | 2/2004 | Zunker et al. ................ 600/29 |
| 6,699,174 B1 | * | 3/2004 | Bennett ....................... 600/29 |
| 6,739,341 B2 | * | 5/2004 | Tihon et al. ................. 128/885 |

* cited by examiner

*Primary Examiner*—Henry Bennett
*Assistant Examiner*—Nihir Patel
(74) *Attorney, Agent, or Firm*—Thomas J. Nikolai; Nikolai & Mersereau, P.A.

(57) ABSTRACT

A kit to facilitate self-placement of an incontinence prevention device within the urethra includes a deployment base member, a deployment tube, a deployment pusher along with the incontinence prevention device in a sterile pack. The base member includes a rigid shaft of a predetermined length having a finger grip member at one end and a hook member at its opposite end. The shaft of the base member is adapted to fit through the lumen of the deployment tube with the hook projecting out from a proximal end of the deployment tube and with the hook engaging a retention loop on the incontinence prevention device when in its sterile package. Upon removal of the kit components, the deployment tube is slid off the deployment base member and, in doing so, the incontinence prevention device becomes loaded into the deployment tube. The pusher is then used to urge the incontinence prevention device from the deployment tube into the urethra.

4 Claims, 7 Drawing Sheets

INCONTINENCE DEVICE INSERTION KIT

CROSS-REFERENCE TO RELATED APPLICATION

This application is a divisional of application Ser. No. 10/146,087, filed May 15, 2002, now U.S. Pat. No. 6,739,341 and entitled "Incontinence Device Insertion Kit".

BACKGROUND OF THE INVENTION

I. Field of the Invention

This invention relates generally to a system for treating female stress incontinence, and more particularly to a kit containing components for facilitating placement of an incontinence prevention device in the female urethra.

II. Discussion of the Prior Art

In my U.S. Pat. No. 6,311,689B1, I describe an incontinence prevention device that comprises a soft, flexible, elastomeric shaft member, preferably silicone, that is sized to fit in the female urethra and which has a retention structure in the form of a closed loop at a distal end of the shaft member that is adapted to cooperate with the bladder neck to prevent the device from being expelled during voluntary urination. The device further includes a proximal wing-like retention structure adapted to cooperate with the vestibule proximate the urethral meatus to prevent upward migration.

In order to insert the incontinence prevention device, a lumen is provided for receiving a straightening stylet therein. With the stylet fully inserted, the distal retention loop is rendered generally rectilinear so as to exhibit a low profile. The tip portion may then be lubricated and the device is inserted by advancing the distal retention structure in its straightened condition on the stylet through the urethral meatus and up the urethra until the distal retention device is resident in the patient's bladder. At this point, the stylet is removed, allowing the loop to reform on the distal end of the shaft.

While the device and method of insertion described in the '689 patent is safe and effective, concern has been expressed by some patients about the use of a stiffening stylet. Some have expressed fear that the stiffening stylet might be made to pierce through the wall defining the stylet lumen, and that it could result in injury to the urethral wall as the incontinence prevention device is being inserted.

It is accordingly a principal object of the present invention to provide a method and apparatus for inserting an incontinence prevention device in the female urethra that does not require the use of a stiffening stylet wire to render the device initially rectilinear for placement within the urethra.

It is a further object of the invention to provide an incontinence prevention device and an insertion mechanism as a kit for use by a patient at home and without the aid of a medical professional.

SUMMARY OF THE INVENTION

The present invention provides a kit for use in treating female stress incontinence. The kit contains an incontinence prevention device having a relatively soft, elastomeric shaft with a closed loop bladder retention structure at a distal end thereof and a vestibule engaging retention structure at its proximal end. The insertion assembly includes a deployment base member having a finger grip at a proximal end thereof and at least one rigid shaft projecting longitudinally from the finger grip. The rigid shaft includes a device engagement element at its distal end. The kit further includes a tubular handle, referred to herein as a deployment tube, for receiving the incontinence prevention device in a lumen thereof at a time immediately prior to deployment of the incontinence prevention device into the urethra. The deployment tube is slidable over the rigid shaft for facilitating loading of the incontinence device into the lumen of the deployment tube. Its diameter is such that the retention loop is collapsed and rectilinear. The kit further contains a plunger that is adapted to fit within the lumen of the deployment tube and which can be used to eject the incontinence device from the deployment tube into the urethra.

The incontinence device can be loaded into the deployment tube a short time prior to self-placement into the urethra so that the retention loop does not take a set, that could preclude the loop retention structure from opening up upon reaching its location in the bladder neck. Moreover, there is no need for the patient to touch the incontinence device itself, thereby maintaining a sterile condition and minimizing the occurrence of infection.

There are, of course, additional features of the invention that will be described hereinafter which will form the subject matter of the appended claims. Those skilled in the art will appreciate that the preferred embodiments may readily be used as a basis for designing other structures, methods and systems for carrying out the several purposes of the present invention. It is important, therefore, that the claims be regarded as including such equivalent constructions since they do not depart from the spirit and scope of the present invention. The foregoing and other features and other advantages of the invention will be apparent from the following more particular description of preferred embodiments of the invention, as illustrated in the accompanying drawings.

DESCRIPTION OF THE PREFERRED EMBODIMENT

Figure 1:
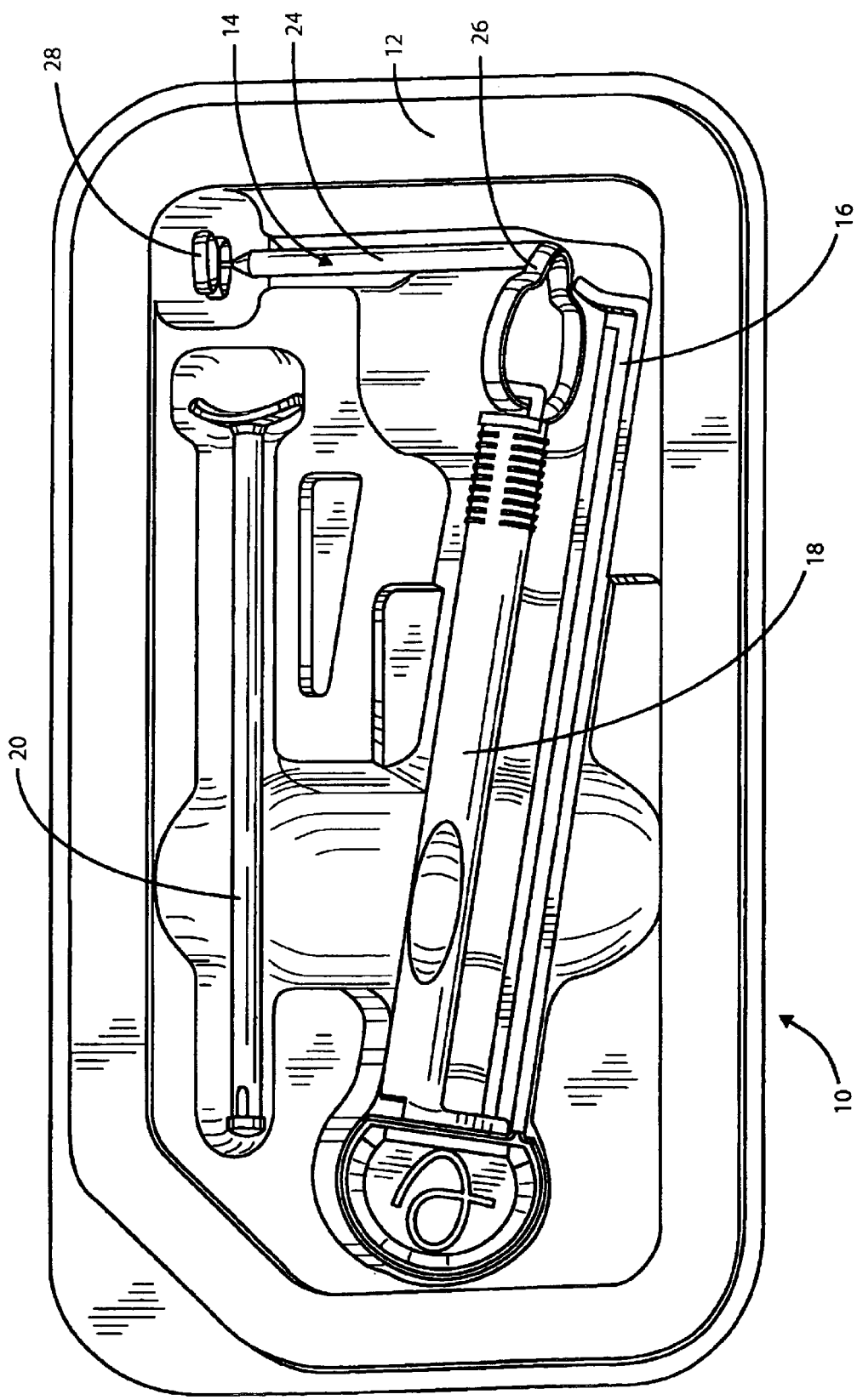
FIG. 1 is a perspective view of a kit comprising the incontinence device and a preferred embodiment of an associated insertion assembly, all contained within a sterile package.

Referring first to FIG. 1, there is shown a component kit 10 comprising a sterile package 12 containing an incontinence prevention device 14, a deployment base member 16, a deployment tube 18 and a pusher plunger 20. The kit may also conveniently contain a supply of a gel lubricant (not shown). Following the sealing of the kit components in the package 12, the package is subjected to a sterilization operation such as by subjecting the package to gamma radiation in a manner well known in the art or by introducing a sterilant such as ethylene oxide into the package.

The incontinence prevention device 14 may be made in accordance with the teachings of my U.S. Pat. No. 6,311,689B1, which is hereby incorporated by reference. It need not, however, have a stylet lumen therein. The device comprises an elongated, soft, elastomeric shaft 24 having an enlarged closed loop 26, also formed from a soft elastomeric material preferably silicone rubber, affixed to the distal end of the shaft 24. A proximal retention member 28 in the form of a wing-like projections, also of a soft material that is configured to conform to the vestibule proximate the urethral opening is disposed on a proximal end of the shaft 24.

Those desiring more detailed information on the size and shape configuration of the incontinence prevention device 14 may derive same from a reading of the aforereferenced '689 patent.

As will be explained in greater-detail hereinbelow, the device 14 may be self-inserted into the urethra by a female subject by first loading the device 14 into the deployment tube 18 in a manner yet to be described and then positioning the distal end of the delivery tube proximate the urethral meatus and expelling the device 14 from the deployment tube 18 using the deployment plunger 20 as a pusher device.

Because the retention loop 26 of the device 14 can, with time, take on a permanent set if packaged with the device 14 already contained within the lumen of the deployment tube 18, it is a feature that the placement of the incontinence prevention device 14 within the deployment tube can be achieved only a relatively short time prior to use of the deployment device to insure that the retention loop 26 will fully expand to its open-loop shape once the loop enters the urinary bladder where it is unconstrained either by the delivery tube 18 or the urethra. It is also important to insure that the device 14 remains sterile and that it does not come in contact with the subject's fingers during the insertion process. The delivery kit 10 of the present invention assures these results.

Figure 2:
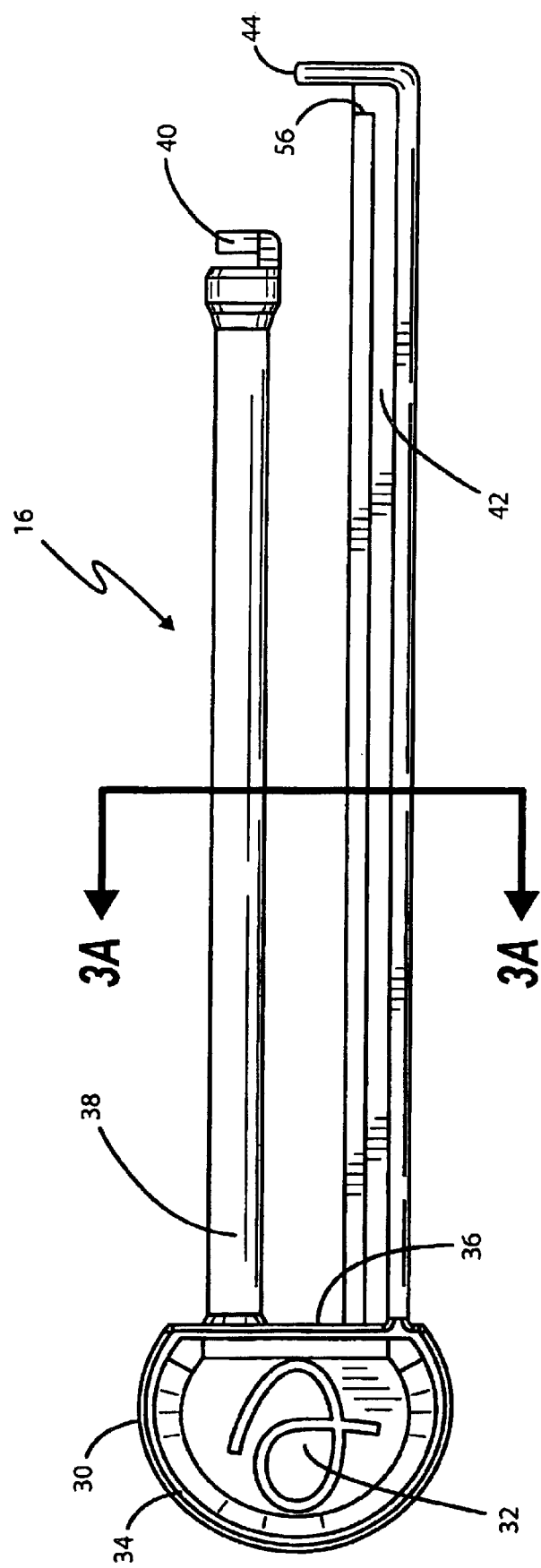
FIG. 2 is a side elevation view of the deployment base member in the embodiment of FIG. 1.

Referring next to FIG. 2, there is shown a side elevation view of the deployment base member 16 of FIG. 1. In the preferred embodiment, it comprises a finger grip element 30 which may be somewhat semi-circular in shape and having a recessed central portion 32 defined by a peripheral wall 34. Having this shape allows the device 16 to be readily gripped between the thumb and forefinger of a user's hand.

Figure 3:
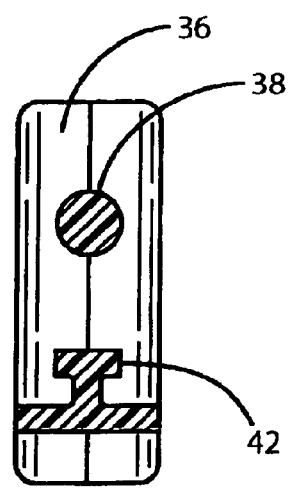
FIG. 3 is a cross-sectional view taken along the line 3—3 in FIG. 2.

Projecting longitudinally from a base 36 of the finger grip element 30 is a longitudinally extending rod 38 having an integrally molded, L-shaped hook as a device engagement element 40 formed at the distal end thereof. In accordance with the embodiment of FIG. 2, the deployment base member 16 further includes a second rigid, longitudinally-extending, rail 42 that has an integrally molded stop member 44 at its distal end. The rail 42 preferably has a somewhat I-shaped cross-section, as best seen in the cross-sectional view of FIG. 3.

The length of the rail 42 is greater than that of the first rigid rod 38 by a predetermined amount. Without limitation, the length of the first rod 38 may be approximately 92.75 mm and the length of the rod 42 may be 107.25 mm.

Figure 4:
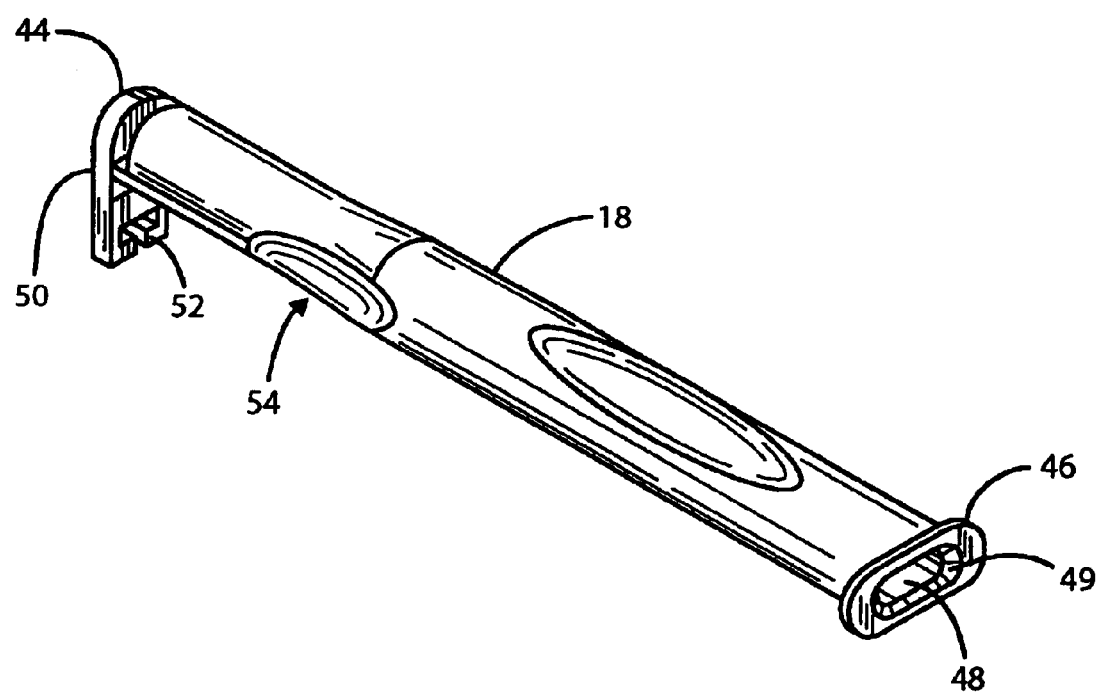
FIG. 4 is a perspective view of the deployment tube contained in the kit of FIG. 1.

Referring now to FIG. 4, it shows a perspective view of the deployment tube 18 of the kit 10. Tube 18 has a distal end 44 and a proximal end 46 with a lumen 48 extending therebetween. Integrally formed with and projecting perpendicularly to the longitudinal axis of the tube 18 at its distal end 44 is an insertion limit 50. The lower end of the insertion limit member 50 includes a T-shaped notch 52. It is dimensioned to engage the guide rail 42 comprising the second rod of the deployment base member 16 when the first rod 38 of the deployment base member 16 is disposed within the lumen 48 of the deployment tube 18. The lumen 48 has a shape to accept the rigid rod 38 therein with sufficient clearance to permit the tube to slide relative to the road 38. Opposed sidewall surfaces of the tube 18 may be slightly indented as at 54 and these surfaces are preferably knurled to facilitate gripping thereof by the user.

To facilitate entry of the retention loop 26 of the incontinence device 14 into the deployment tube 18, it has been found expedient to provide a flared or oval opening on the proximal end of the deployment tube where the opening has a chamfered edge 49. This shape on the distal end of the deployment tube causes the retention loop 26 to compress into two contiguous parallel, rectilinear segments as it is being drawn by the hook-shaped device engagement element 40 into the lumen 48 of the deployment tube. Further, the lumen of the deployment tube may also be of an oval cross-section throughout its length or may transition to a circular cross-section at a predetermined point along the length thereof as reflected in FIG. 4.

Figure 5:
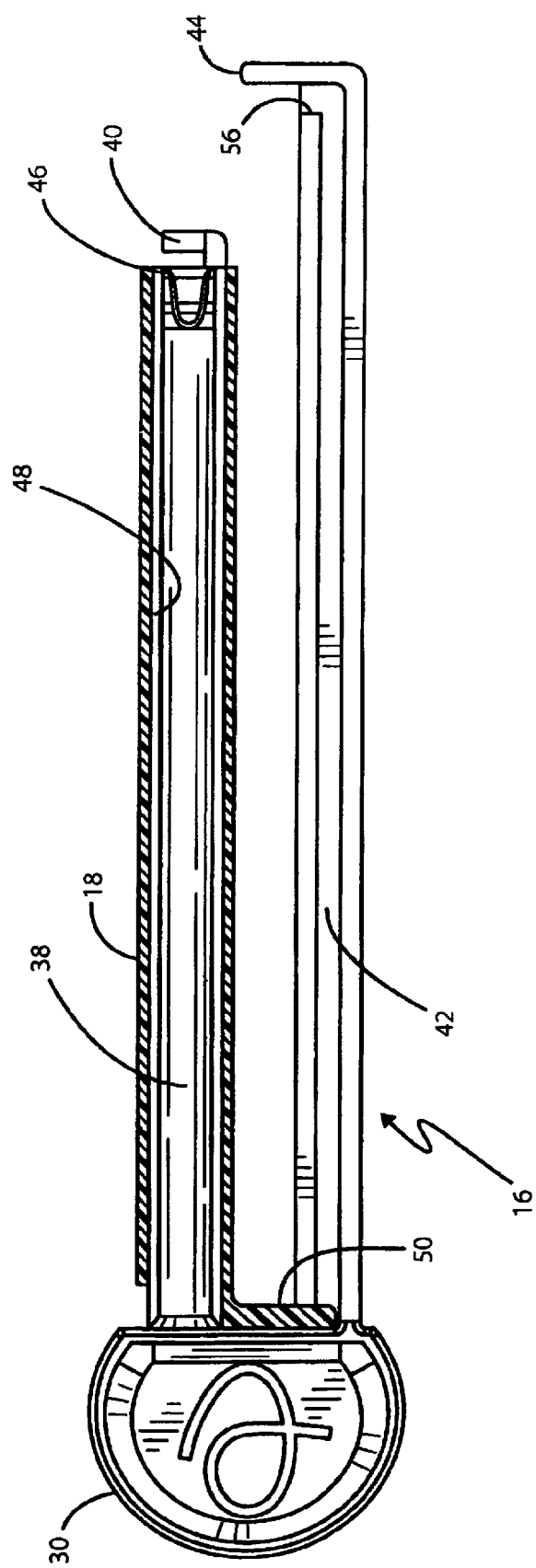
FIG. 5 is a partial cross-sectional view of the deployment tube mounted on the deployment base member prior to use.

The cross-sectional view of FIG. 5 shows the deployment tube 18 in surrounding relationship to the first rod 38 of the deployment base member 16. Here it can be seen how the T-shaped notch 52 on the retention limit member 50 engages the guide rail 42. Also visible in the view of FIG. 5 is the fact that the length of the deployment tube 18 is slightly less than the length of the first rod 38 such that the hook-shaped engagement element 40 extends outward from the distal end 46 of the deployment tube.

In loading the incontinence device 14 into the deployment tube 18, the device comes packaged with the loop 25, fitted over the hook-shaped element 40 in the space between the element 40 and the proximal end 46 of the deployment tube. That is to say, the kit comes with the loop 26 encircling the L-shaped hook element 40, thus obviating the need for the users to touch the sterilized device 14. Now, when the finger grip 30 is grasped between the thumb and foregoing of the user's one hand and the thumb and forefinger of the other hand are placed on the surfaces 54 of the deployment tube, the deployment tube may be slid in the distal direction causing the retention loop to be drawn into the lumen 48 of the deployment tube as the retention limit 50 slides along the I-shaped guide rail 42 of the base member 16. The deployment tube is slid in the distal direction until the retention limit member 50 comes into abutment with the stop member 44 on the rail 42, at which point only a predetermined portion of the retention loop 26 will extend out beyond the distal end of the deployment tube 18, given the difference in length of the cylindrical rod 38 and the guide rail 42. The extending portion is still maintained rectilinear in that the remainder of the loop is still constrained by the wall of the deployment tube. The described incontinence device loading system also assures proper orientation of the loop as it expands upon entry into the bladder. With the aid of the L-shaped hook, the loop exits the lumen of the deployment tube in the same orientation as it had upon entry into the proximal end of the tube.

Because the guide rail 42 has its upper flange notched, as at 56, when the retention limit member 50 reaches the stop 44, the guide tube with the incontinence prevention device contained therein can be lifted free of rail 42 of the deployment base member 16.

Figure 6:
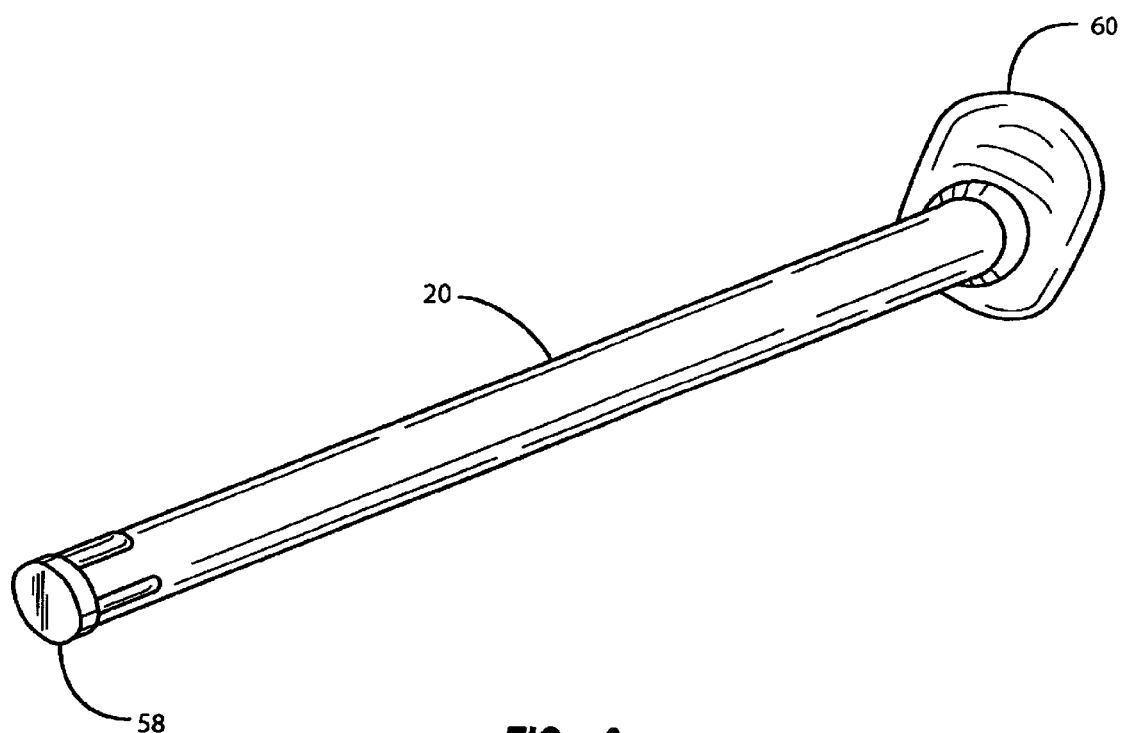
FIG. 6 is a perspective view of the deployment pusher.
Figure 7:
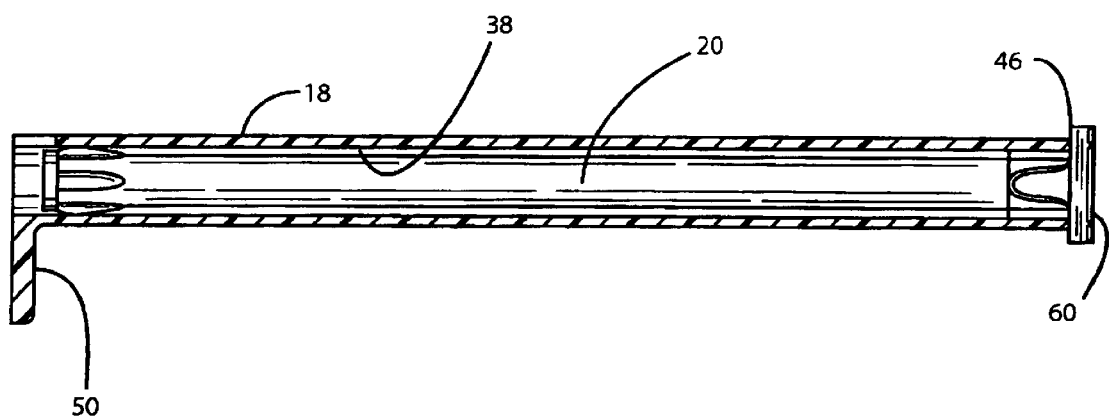
FIG. 7 is a cross-sectioned side view of the deployment tube with the pusher member inserted fully therein.

Next, the portion of the retention loop projecting outward from the distal end of the deployment tube can be dipped into a sterile lubricating gel which may come with the kit and the user will next insert the distal end 58 of the plunger 20 (FIG. 6) into the lumen 48 at the proximal end 46 thereof and will then insert the protruding portion of the retention loop into the urethral meatus until the insertion limit member 50 is brought into contact with the subject's vestibule. The insertion limit member 50 is sufficiently large to prevent the deployment tube from passing through the meatus. Now, by depressing the finger rest 60 of the plunger 20, the incontinence prevention device is forced out from the deployment tube 18 and through the urethra until the finger rest 60 of the plunger abuts the end 46 of the deployment tube as shown in FIG. 7. The length of the plunger is judiciously chosen such that when fully inserted, the retention loop will be disposed within the subject urinary bladder where it can expand to its open loop shape for nesting in the bladder neck.

The deployment base member, deployment tube and pusher may be molded from a suitable medical grade plastic, such as ABS, but limitation to this material is not to be inferred.

Figure 8:
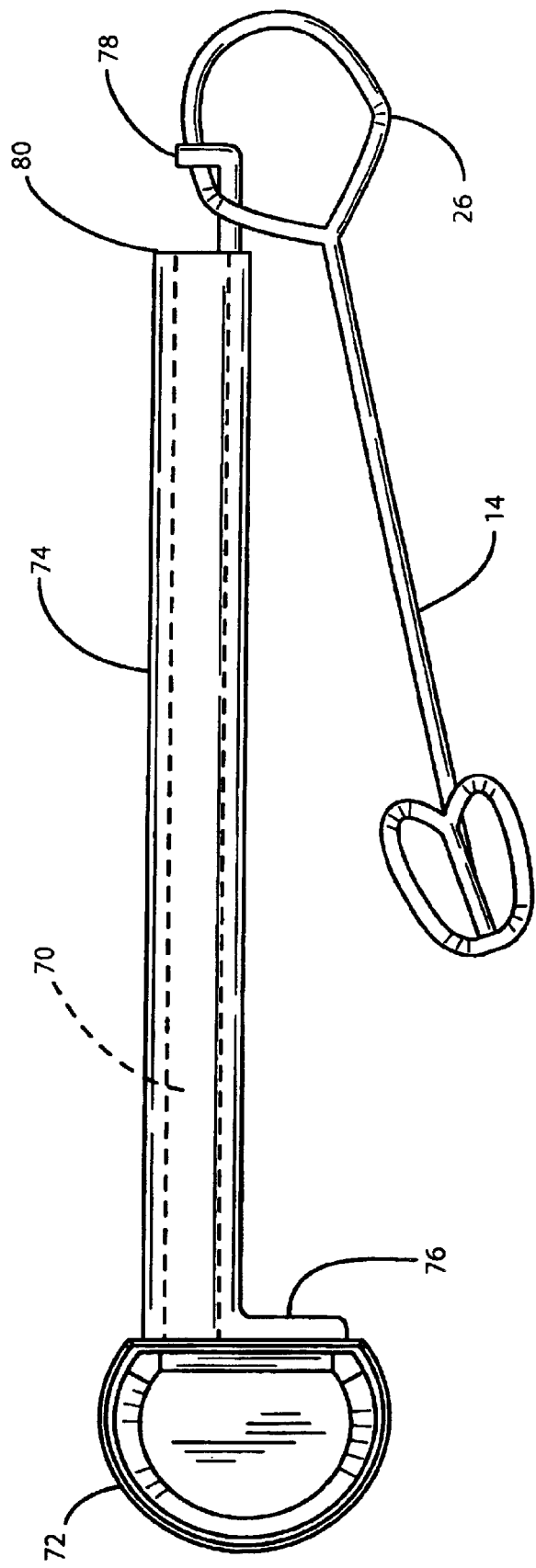
FIG. 8 is a perspective view of an alternative embodiment of the present invention.

FIG. 8 illustrates an alternative embodiment of the deployment device of the present invention. Here, the deployment base member includes only a single longitudinally extending rod 70 that is affixed to and projects from the finger grip member 72. Fitted over the rod 70 is a deployment tube 74 that has a stop member 76 at a distal end thereof. The rod 70 terminates in a hook 78 that extends outwardly beyond the distal end 80 of the deployment tube 74 when the stop 76 is in abutment with the base of the finger grip member 72. An incontinence prevention device of the type already described is shown with its retention loop 26 looped over the hook 78. The configuration shown in FIG. 8 would be packaged in a sterile container with the hook 78 engaging the loop 26.

When removed by the user from the sterile package, she would grasp the finger grip 72 between the thumb and forefinger of one hand and the deployment tube 74 between the thumb and forefinger of the other hand and then slide the deployment tube 74 to the right as shown in FIG. 8, drawing the retention loop 26 and the stem 14 into the deployment tube 74. Instructions with the device would advise the user to uncouple the hook from the loop once a portion of the loop, approximately 15 mm in length, is projecting from the distal end of the deployment tube. As before, the projecting portion of the loop remains collapsed and rectilinear. It would be dipped in a lubricant and the deployment tube positioned such that the lubricated tip of the retention loop is inserted into the urethral meatus and the stop 76 abuts the user's vestibule. A pusher, like that shown in FIG. 6, is again used to move the incontinence prevention device out of the deployment tube and through the urethra until the retention loop 26 enters the urinary bladder and expands to its open loop configuration.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself. For example, a piece of string could be substituted for the deployment base member hook where the string loops through the retention loop of the incontinence prevention device and through the lumen of the deployment tube. Immediately prior to deployment, by pulling on the string, the incontinence prevention device will be drawn into and through the deployment tube with a portion of the retention loop extending beyond the end of the deployment tube as earlier described.

What is claimed is:

1. A kit for use in treating female stress incontinence comprising:

(a) an incontinence device having a relatively soft, elastomeric shaft with a bladder retention structure at a distal end thereof and a vestibule engaging retention structure at a proximal end thereof;

(b) a deployment base member having a finger grip at a proximal end thereof and a first shaft projecting longitudinally from the finger grip, the first shaft including an element at a distal end thereof to engage the device;

(c) a deployment tube adapted to receive the incontinence device in a lumen thereof at a time immediately prior to deployment of the incontinence device into the urethra, said deployment tube being slidable over the first shaft for facilitating loading of the incontinence device into said lumen; and (d) a plunger adapted to fit within said lumen for ejecting the incontinence device from the deployment tube into the urethra.

2. The kit of claim 1 wherein the element comprises a hook.

3. A sterilized kit for use in treating female stress incontinence comprising:

(a) an incontinence device having a relatively soft, elastomeric shaft with a closed bladder retention loop at a distal end thereof;

(b) a deployment tube having first and second ends for receiving the incontinence device in a lumen thereof at a time just prior to deployment of the incontinence device into a urethra of a subject;

(c) a means for drawing the incontinence device, retention loop first into a said first end and through said lumen until a predetermined portion of the retention loop extends outward of said second end while maintaining sterility thereof; and (d) a pusher member insertable through said first end of the deployment tube for forcing the incontinence device out from the second end and through the subject's urethra.

4. A sterilized kit for use in treating female stress incontinence comprising:

(a) an incontinence device having a relatively soft, elastomeric shaft with a closed bladder retention loop at a distal end thereof;

(b) a deployment tube having first and second ends for receiving the incontinence device in the lumen thereof, said deployment tube including an insertion limit member at the second end; and (c) a pusher member insertable through the first end of the deployment tube for forcing the incontinence device out from the second end and through the subject's urethra, the insertion limit member preventing entry of the deployment tube into the urethra.

* * * * *